United States Patent
Norris

(10) Patent No.: US 10,765,861 B2
(45) Date of Patent: Sep. 8, 2020

(54) APPARATUS AND METHOD FOR TREATING CANCER CELLS AND BACTERIA IN MAMMALS INCLUDING HUMANS

(71) Applicant: BNR Technology Development, LLC, Conroe, TX (US)

(72) Inventor: Jeffrey B. Norris, Montgomery, TX (US)

(73) Assignee: BNR Technology Development, LLC, Conroe, TX (US)

( * ) Notice: Subject to any disclaimer, the term of this patent is extended or adjusted under 35 U.S.C. 154(b) by 775 days.

(21) Appl. No.: 15/387,513

(22) Filed: Dec. 21, 2016

(65) Prior Publication Data

US 2017/0100584 A1    Apr. 13, 2017

Related U.S. Application Data

(62) Division of application No. 14/219,073, filed on Mar. 19, 2014, now abandoned.

(60) Provisional application No. 61/805,583, filed on Mar. 27, 2013.

(51) Int. Cl.

| A61N 1/20 | (2006.01) |
|---|---|
| A61B 18/14 | (2006.01) |
| A61C 19/06 | (2006.01) |
| A61L 31/02 | (2006.01) |
| A61L 31/08 | (2006.01) |
| A61N 1/04 | (2006.01) |
| A61N 1/05 | (2006.01) |
| A61B 18/12 | (2006.01) |

(52) U.S. Cl.
CPC .............. *A61N 1/205* (2013.01); *A61B 18/14* (2013.01); *A61C 19/06* (2013.01); *A61L 31/022* (2013.01); *A61L 31/088* (2013.01); *A61N 1/0408* (2013.01); *A61N 1/0476* (2013.01); *A61N 1/0548* (2013.01); *A61B 2018/1266* (2013.01)

(58) Field of Classification Search
CPC ....... A61N 1/20; A61N 1/205; A61N 18/1266
See application file for complete search history.

(56) References Cited

U.S. PATENT DOCUMENTS

| 4,695,472 A | 9/1987 | Dunn et al. |
|---|---|---|
| 5,304,207 A | 4/1994 | Stromer |
| 5,670,198 A | 9/1997 | Reznik et al. |
| 5,948,733 A | 9/1999 | Yoshida et al. |
| 6,032,077 A | 2/2000 | Pomeranz |
| 6,366,808 B1 | 4/2002 | Schroeppel |

(Continued)

OTHER PUBLICATIONS

Hsu, Jack; "Electrical Current Needed to Kill a Human" (Year: 2000).*

(Continued)

*Primary Examiner* — Ronald Hupczey, Jr.
(74) *Attorney, Agent, or Firm* — Tumey L.L.P.

(57) ABSTRACT

Bacteria, cancer cells, fungus and other harmful cells located beneath the surface of a mammal body can be effectively destroyed by passing an electrical current through the area to be treated. Electrodes are positioned on either side of the area to be treated, for example, gums, fingers, arms, legs, feet and torso, and an electric current is caused to flow between the electrodes and through the area to be treated. The electric current will destroy the bacteria, cancer cells, fungus or other harmful cells.

3 Claims, 1 Drawing Sheet

(56) References Cited

U.S. PATENT DOCUMENTS

| | | | |
|---|---|---|---|
| 7,079,890 B2 | 7/2006 | Aker et al. | |
| 7,740,650 B2 | 6/2010 | Brogan et al. | |
| 7,837,719 B2 | 11/2010 | Brogan et al. | |
| 2002/0077676 A1 | 6/2002 | Schroeppel et al. | |
| 2005/0028679 A1 | 2/2005 | Williamson | |
| 2005/0154436 A1 | 7/2005 | Specht et al. | |
| 2005/0187581 A1 | 8/2005 | Hara et al. | |
| 2005/0222646 A1 | 10/2005 | Kroll et al. | |
| 2007/0125642 A1 | 6/2007 | Perry | |
| 2008/0071265 A1 | 3/2008 | Azure | |
| 2009/0117513 A1* | 5/2009 | Nemeh | A61C 19/063 433/32 |

OTHER PUBLICATIONS

Giovinazzo, Paul; "The Fatal Current" (Year: 1987).*

Zeit, F. Robert, "Effect of Direct, Alternating, Tesla Currents and X-Rays on Bacteria", 1901, Journal of American Medicine, vol. 37, 1432-1442 (Year: 1901).*

USPTO Final Office Action for U.S. Appl. No. 14/219,099 dated Jun. 18, 2015.

USPTO Office Action for U.S. Appl. No. 14/219,099 dated Sep. 24, 2014.

USPTO Office Action for U.S. Appl. No. 14/219,099 dated May 20, 2016.

International Search Report and Written Opinion for PCT/US14/31988 dated Sep. 4, 2014.

"Pretreatment Capabilityes and Benefits of Electrocoagulation" by Michael Mickley, Boulder Colorado, Dec. 2004.

USPTO Office Action for U.S. Appl. No. 15/380,862 dated Jul. 25, 2019.

USPTO Final Office Action for U.S. Appl. No. 14/219,073 dated Sep. 22, 2016.

USPTO Office Action for U.S. Appl. No. 14/219,073 dated May 3, 2016.

International Preliminary Report on Patentability for Application No. PCT/US2014/031988 dated Sep. 29, 2015.

USPTO Final Office Action for U.S. Appl. No. 15/380,862 dated Nov. 6, 2019.

* cited by examiner

APPARATUS AND METHOD FOR TREATING CANCER CELLS AND BACTERIA IN MAMMALS INCLUDING HUMANS

This application is a divisional application of U.S. patent application Ser. No. 14/219,073 filed Mar. 19, 2014 which claims priority to U.S. provisional application Ser. No. 61/805,583 filed on Mar. 27, 2013.

BACKGROUND OF INVENTION

1. Field of the Invention

This invention relates to the destruction of cancer and bacteria cells and other harmful cells at various locations within the human body by generating an electrical current between two electrodes such that the current passes through the portion of the body in which bacteria or other harmful cells reside.

2. Description of Related Art

The ability to kill bacteria, cancer cells, fungus and mold spores by utilizing an electrolytic cell has been known for many years. Utilizing an anode and a cathode in a container of water and supplying an AC or DC current to the anode and cathode, the cells between the electrodes have been destroyed. The prevailing wisdom says that the current upsets the osmotic balance of the bacteria cell and causes the cell to either implode or explode. This destruction has been verified by many studies that are readily available to the public. See for example, U.S. Pat. No. 5,948,733 to Yoshida et al issued Sep. 7, 1999 and "Pretreatment Capabilities and Benefits of Electrocoagulation" by Michael Mickley, Boulder Colo., December 2004.

Additionally, Patent Publication No. 2009/0117513A1, published May 7, 2009 discloses that low direct current between two electrodes positioned on opposite sides of teeth gums in the human mouth is effective to kill bacteria as well as viruses and fungus. Similarly, U.S. Pat. No. 7,837,719 to Brogan et al issued Nov. 23, 2010, discloses that toenail fungus can be destroyed by placing one or both feet in a container filled with a solution and passing a low current over and around the toes and nails. The current is created by electrodes positioned within the container.

With respect to cancer cells, studies have shown that low current flow between electrodes implanted within the body is effective in treating cancer cells. See for examples, U.S. Pat. No. 6,366,808 to Schroeppel et al, issued Apr. 2, 2002 and U.S. Pat. No. 7,079,890 to Aker et al, issued Jul. 18, 2006.

These prior art medical devices utilize very low current levels and are only effective to destroy surface bacteria and or viruses but are not effective to penetrate deeper into human tissue to kill bacteria and or viruses located beneath the surface or skin level without implantation.

BRIEF SUMMARY OF THE INVENTION

The present invention is the destruction of bacteria molds or cancer cells below the surface level of the human body by creating an electric current between two electrodes which are positioned externally between the areas of the body to be treated. The electric current is confined between the two electrodes and thus does not injure other areas of the body.

Tests have been done using beef hamburger meat over an inch thick and applying a DC current across the meat with a given amount of bacteria throughout the entire thickness of the meat. After analysis, it was proven that the bacteria in the middle of the meat were destroyed without changing the temperature of the meat. This test was conducted several times to arrive at the best power settings to assure the destruction of the bacteria at a given thickness. More voltage is required to penetrate a thicker sample of meat than that of a thinner piece. It was found that the required amps would be fairly constant but more voltage would be required to achieve the amps in thicker samples of meat.

BRIEF DESCRIPTION OF THE SEVERAL VIEWS OF THE DRAWING(S)

DETAILED DESCRIPTION OF THE INVENTION

Figure 1:
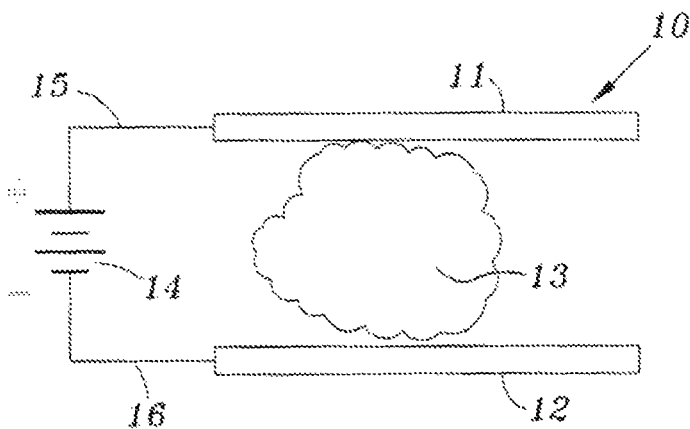
FIG. 1 is a schematic view of an embodiment of an apparatus suitable for carrying out an embodiment of the invention.

FIG. 1 is a schematic view of device suitable for carrying out an embodiment of the invention. A pair of electrodes 11 and 12 are connected to the opposite poles of a power source 14 which may be a variable power output source. The power source is preferable a DC power source. The electrodes can be made of any known material suitable for electrodes such as stainless steel, but preferably are constructed as a base plate made of titanium with a ruthenium or other noble coatings. The size and shape of the electrodes will depend upon the area of the body to be treated and could include curved surfaces and plates that have been curved for positioning around a finger, arm or leg for example.

Electrodes 11 and 12 are positioned exteriorly on either side of the area of the body to be treated as figuratively illustrated at 13. Power source can then be activated and the power adjusted in order to provide an effective amount of current to pass through body mass 13 so as to destroy the bacteria in the area to be treated.

Figure 3:
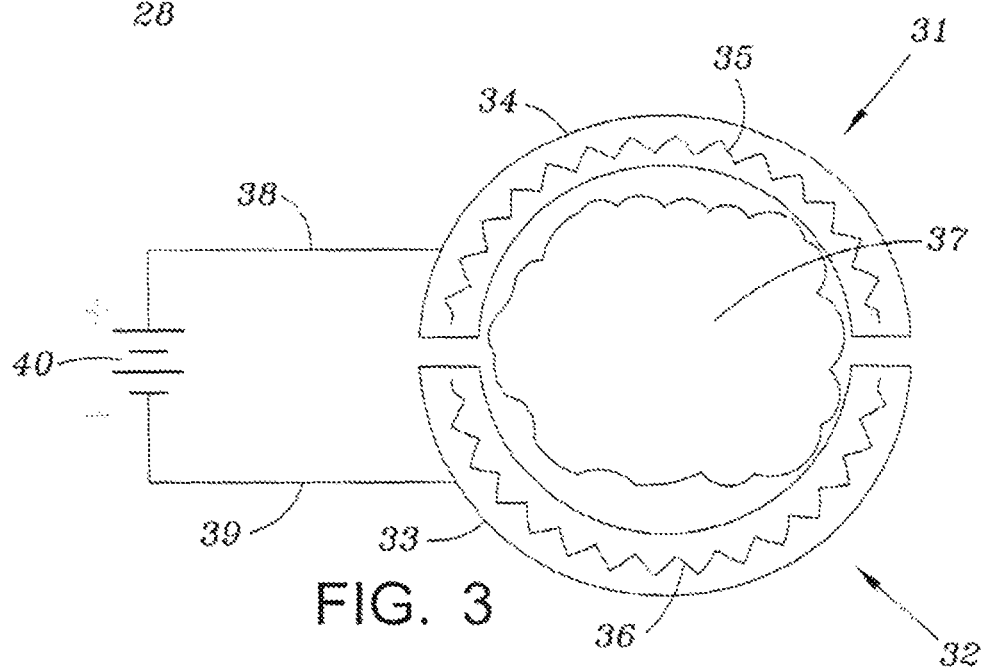
FIG. 3 is a schematic view of a second embodiment according to the invention.

In an alternative arrangement shown in FIG. 3, non-rigid electrodes 31 and 32 could be a wire mesh or any porous substance arrangement 35 and 36 in a protective bag, cloth or other suitable material 33 and 34. The electrodes can be saturated with a brine solution of water to facilitate the transfer of the electricity from the electrode to the area of the body 37 being treated. The wire mesh or porous material can be stainless steel or other suitable conductive material but using a noble electrode made of titanium with a ruthenium coating is preferred. In either arrangement, a layer of water between the electrodes or a cloth wrap or sponge will protect the body from making contact with the electrodes.

Figure 2:
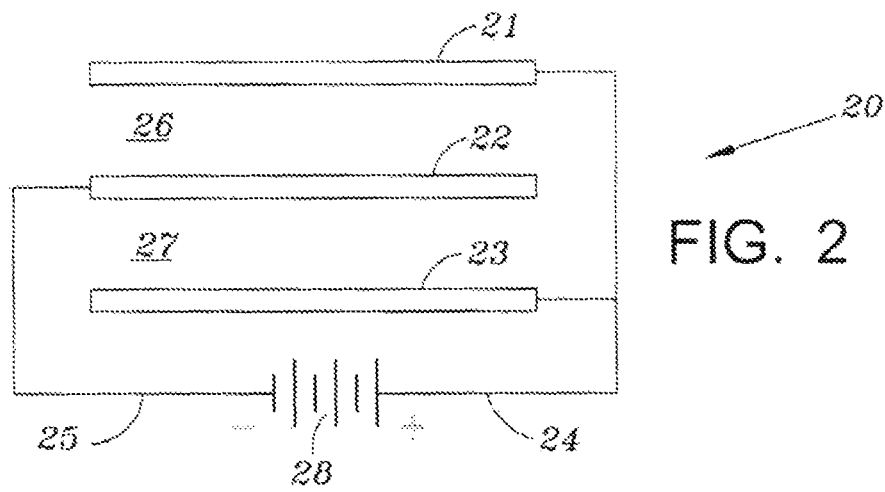
FIG. 2 is a schematic view of an embodiment of the invention suitable for treating foot disorders.

FIG. 2 illustrates an embodiment of an apparatus for treating feet. In this embodiment three elongated electrodes 21, 22 and 23 are positioned within a container. Electrodes 21, 22 and 23 are long enough to cover the entire foot length and high enough to cover the foot up to about ankle height. The patient's feet are positioned between the plate electrodes as shown at 26 and 27. Plates 21 and 23 are connected to one pole of the power sources via lead 24 and electrode 22 is connected to the opposite pole by lead 25. In operation a conductive solution is placed in the container and the patient's feet are positioned at 26 and 27. The power source is energized and can be adjusted so that an effective amount of current flows between the electrodes to destroy bacteria and or fungus below the toe nails.

The range of current for the foot bath type of device is from 0.5 amps to 6 amps. Higher current will be utilized to penetrate deeper to treat diseases under the skin.

In the case of wire mesh pads and the embodiment of FIG. 1, the range will range from 0.05 amps up to 6 amps depending on the thickness of the extremity being treated. The voltage will vary depending on the conductivity of the extremity which will determine how many volts will be required to push the required amps through the extremity.

Example 1

Treatment of abscessed tooth utilizing dc current to kill the associated bacteria which caused great pain due to the infection in the root of the tooth. Pain is the most common system of needing a root canal. The paining from this condition is fairly specific. If the tooth is still alive, it will become extremely sensitive to hot or cold water. This pain can continue day and night and an abscess will form when the pulp of the tooth dies and a pus pocket forms around the end of the root. The pus accumulates in an area of dead nerve tissue that is infected with bacteria. Although antibiotics can help the bacteria from spreading to other surrounding teeth and gums, a root canal will be required to clean out all the dead tissue and bacteria inside the pulp inside the root canal.

The root canal cannot be performed while there is still an infection in the tooth due to bacteria. Antibiotics must be taken for up to 10 days before the infection is cleared and before the root canal can be performed. During these 10 days the pain will continue day and night until antibiotics can destroy the bacteria and lesson the pain. This pain can continue for days until controlled.

Two patients who were diagnosed with an abscessed tooth both of which had tremendous pain were treated with a bacteria treatment device according to the invention which includes a positive and negative electrode which are inserted in the mouth and placed on either side of the infected tooth. The positive electrode was placed on one side and the negative placed on the opposite side. This placement is to assure that dc current can pass through the entire tooth and gum area of the selected tooth. The electrodes are made of titanium plates with ruthenium coating or other similar noble metal and are covered with a sponge type material for comfort wetted with a saline solution to enhance current flow to the tooth and gums.

Both patients were subjected to 0.1 and 0.4 of an amp with voltage being varied as to the thickness of the gums. This treatment was held for approximately 3 minutes but more or less may be required. The goal was to destroy the bacteria thus relieving the pain quickly in lieu of waiting days for the pain to subside. Some patients cannot take the strong pain medication due to other health issues and must face the pain until the antibiotics clear the infection. This procedure can also shorten the time which a root canal can be accomplished when a dental x-ray confirms the infection is gone.

Both patients noted that the pain was diminished right away and all pain relieved within a couple of hours. Both patients eventually had the root canals done at their convenience.

Example 2

A 50 year old patient was referred to a podiatrist with a fungal growth on his toes. The doctor noted a visible fungal growth on the patient's feet and a biopsy was taken. The pathology report which was received in the doctors off was as follows:

Diagnosis: Nail plate and attached superficial nail bed, right hallux, biopsy showed PAS reaction demonstrates probably dermatophytes. Moderate fungal growth is observed. Onychomycosis, sub fungal pattern.

Treatment: The patient was treated using an anode and cathode device which is placed over each toe with one electrode on the top of the toe and the other electrode on the bottom of the toe. This arrangement allows the direct current when applied to flow through the toe to destroy the fungus. The toes were treated utilizing voltages ranging from 9 volts to 32 volts depending on the size of the toe. Time of treatment was approximately 5 minutes per toe.

A post treatment biopsy was taken by the attending doctor.

Post treatment biopsy results: A PAS reaction and GMS stain fail to demonstrate fungal elements. It was shown that treatment of this fungus using DC current with specific applied voltages was very successful.

All treatment was conducted under a doctor's care in the doctor's office.

Example 3

Infected acne or boils can occur when a hair follicle becomes plugged with oil or dirt and then becomes infected with bacteria. In most cases these areas are just under the skin and are easily treated with spaced electrodes as disclosed herein.

Patient with infected acne on facial cheek: The patient had a very painful rising on his left cheek that was very red and stood out on his face.

The patient was given a device which resembles a large clothes pin where one surface is a stainless positive electrode and the opposite surface was stainless negative electrode. The electrodes were connected to a DC current power supply capable of supplying 0.1 to 0.9 amps with varied voltage. The patient was able to clamp the two electrodes over the infected area and then gradually increase voltage/amps until the amount of current becomes uncomfortable then the power is dialed back to a level that could be tolerated. The power was left on for approximately 60 seconds.

Results: By the end of the day the pain had subsided and the soreness was better. By the next morning, the area was no longer swollen and the soreness was totally gone. Two days later, there was no sign of the infected area. The DC current had penetrated under the skin and destroyed the bacteria allowing a healing process to begin.

Although the present invention has been described with respect to specific details, it is not intended that such details should be regarded as limitations on the scope of the invention, except to the extent that they are included in the accompanying claims.

I claim:

1. A method of killing bacteria in an area of roots the root of a tooth in a mammal comprising:
   a) positioning a first electrode adjacent a first side of a gum area where the tooth is located,
   b) positioning a second electrode adjacent a second side of the gum area where the tooth is located such that the root area of the tooth is positioned between the first and second electrodes,
   c) connecting a power source to the electrodes; and d) energizing the power source to a sufficient voltage to cause current to flow from the first electrode, through the root area and the root of the tooth containing the bacteria, and to the second electrode, wherein the current passing through the root area and tooth root is between 0.1 and 0.4 amps.

2. The method of claim 1 wherein the power source is a direct current power source.

3. The method of claim 1 wherein the current is applied for approximately 3 minutes.

* * * * *